United States Patent
Mayeaux

(10) Patent No.: US 6,904,816 B2
(45) Date of Patent: Jun. 14, 2005

(54) SYSTEM FOR RETRIEVING A GAS PHASE SAMPLE FROM A GAS STREAM CONTAINING ENTRAINED LIQUID, AND SAMPLE CONDITIONER ASSEMBLY THEREFORE

(76) Inventor: Donald P. Mayeaux, 18632 Manchac Dr., Prarieville, LA (US) 70769

( * ) Notice: Subject to any disclaimer, the term of this patent is extended or adjusted under 35 U.S.C. 154(b) by 0 days.

(21) Appl. No.: 10/408,026

(22) Filed: Apr. 3, 2003

(65) Prior Publication Data

US 2003/0233890 A1 Dec. 25, 2003

Related U.S. Application Data

(60) Division of application No. 09/915,192, filed on Jul. 25, 2001, now Pat. No. 6,701,794, and a continuation-in-part of application No. 09/162,239, filed on Sep. 28, 1998, now Pat. No. 6,357,304, which is a continuation-in-part of application No. 08/701,406, filed on Aug. 22, 1996, now Pat. No. 5,841,036.
(60) Provisional application No. 60/221,335, filed on Jul. 26, 2000.

(51) Int. Cl.[7] ............................. G01N 1/20; G01N 1/22; G01N 1/28; G01N 1/18
(52) U.S. Cl. ............................... 73/863.23; 73/863.12; 73/863.81; 73/31.07
(58) Field of Search ......................... 73/863.11–863.25, 73/863, 863.81, 863.85, 863.86, 29.01, 31.07

(56) References Cited

U.S. PATENT DOCUMENTS

3,835,710 A * 9/1974 Pogorski .................. 73/864.74
5,442,969 A * 8/1995 Troutner et al. ..... 73/863.85 X
2004/0168526 A1 * 9/2004 Mayeaux ................. 73/863.23

OTHER PUBLICATIONS

A+ Corporation, "Series 100 Genie Membrane Separators", Aug. 1998, pp. 1–7.*

* cited by examiner

Primary Examiner—Thomas P. Noland
(74) Attorney, Agent, or Firm—Joseph T Regard Ltd, (plc)

(57) ABSTRACT

A system for the retrieval and initial conditioning of sample gas for "on line" analyzers or filling of gas sample cylinders. The preferred embodiment of the present invention contemplates a system configured to obtain a representative gas phase sample from a process gas containing entrained liquid, or a process gas which generally is highly susceptible to partial condensation of some gas phase components. The preferred embodiment of the present invention teaches an assembly including a phase separation membrane and housing configured to facilitate the removal of entrained liquid from a sample gas stream. Accuracy of the sample is enhanced, and compositional changes are avoided by first extracting a sample from the process gas followed by removal of entrained liquid it may contain, with the entrained liquid removal being conducted at the prevailing process gas pressure and temperature. Thereafter the liquid free sample may be desaturated by lowering its pressure to reduce its susceptibility to condensation.

9 Claims, 18 Drawing Sheets

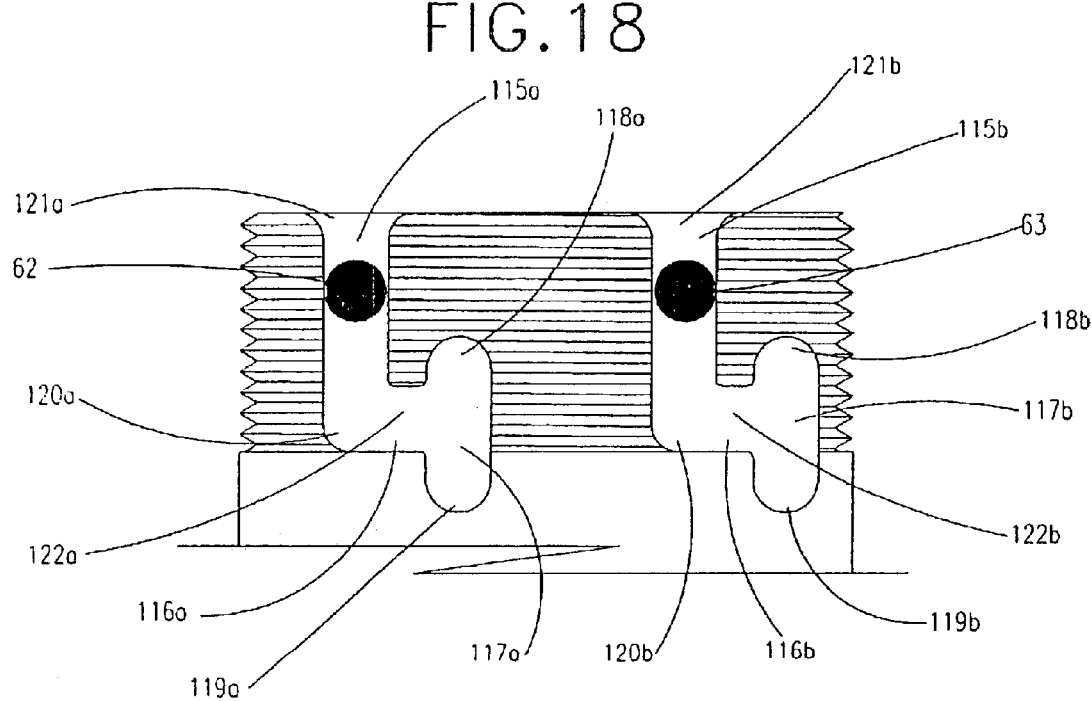

SYSTEM FOR RETRIEVING A GAS PHASE SAMPLE FROM A GAS STREAM CONTAINING ENTRAINED LIQUID, AND SAMPLE CONDITIONER ASSEMBLY THEREFORE

REFERENCE TO RELATED APPLICATIONS

The present application is a Divisional of U.S. Utility Application of Ser. No. 09/915,192 filed Jul. 25, 2001 now U.S. Pat. No. 6,701,794, which claims the benefit of U.S. provisional application Ser. No. 60/221,335 filed Jul. 26, 2000, and is also a continuation-in-part of U.S. patent application Ser. No. 09/162,239, filed Sep. 28, 1998 now U.S. Pat. No. 6,357,304, entitled "System for Retrieving a Gas Phase Sample from a Gas Stream containing Entrained Liquid, and Sample Conditioner Assembly Therefore", which application is a continuation-in-part of U.S. patent application Ser. No. 08/701,406, filed Aug. 22, 1996 now U.S. Pat. No. 5,841,036, entitled "Modular Sample Conditioning System.

TECHNICAL FIELD OF THE INVENTION

The present invention relates to the sampling of process fluids such as implemented by petrochemical plants, refineries, gas separation plants, natural gas pipelines, etc, and in particular to the collection and initial conditioning of sample gas for "on line" analyzers or filling of gas sample cylinders.

The preferred embodiment of the present invention contemplates a system configured to obtain a representative gas phase sample from a process gas containing entrained liquid, or a process gas which generally is highly susceptible to partial condensation of some gas phase components.

The preferred embodiment of the present invention teaches an assembly including a phase separation membrane and housing configured to facilitate the removal of entrained liquid from a sample gas stream. Accuracy of the sample is enhanced, and compositional changes are avoided by first extracting a sample from the process gas followed by removal of entrained liquid it may contain, with the entrained liquid removal being conducted at the prevailing process gas pressure and temperature. Thereafter the liquid free sample may be desaturated by lowering its pressure to reduce its susceptibility to condensation.

BACKGROUND OF THE INVENTION

The heating value of natural gas has a significant impact on its monetary value. In general, the heating value of natural gas increases as the concentration of low volatility, high molecular weight components increases. Condensation of gas phase components, which reduce the proportion of high molecular weight components, therefore tends to decrease gas phase heating value while vaporization of entrained liquid has the opposite effect.

In order for natural gas supply to balance with demand over the next 10 to 20 years it will be necessary to increase production from deep-water fields in the Gulf of Mexico. (Refer to Volume 1, Fall/Winter 1997 official newsletter of Colorado Engineering Experiment Station Inc.) Gas produced from deep-water fields, containing higher concentrations of low volatility components such as water vapor and heavy hydrocarbons, has a higher susceptibility to condensation than shelf and onshore production gas. Additionally, some onshore produced gas, particularly in low ambient temperature regions, frequently contain entrained liquids.

Other liquids which can influence vapor phase composition when fluid pressure or temperature changes occur are glycols and amines which are carried over into the gas phase from gas contactors designed to remove water vapor and acid gases respectively.

A Joint Industry Project (JIP) is underway to address problems associated with measurement and transportation of "wet gases". A part of the JIP focus will include improvement of wet gas sampling techniques.

The American Petroleum Institute (API) and the Gas Processors Association (GPA) are two leading industry organizations having recommended standard practices for sampling and analysis of natural gas. Both recommend that entrained liquids are to be removed from natural gas samples at prevailing source gas pressure and temperature. (Refer to Manual of Petroleum Measurement Standards chapter 14—Natural Gas fluids measurement, section 1 collecting and handling natural gas samples for custody transfer, fourth edition, August 1993.) This is done to prevent gas phase compositional changes caused by vaporization and condensation.

Following the recommended practices has been almost impossible due to lack of available hardware to accomplish the task. For example GPA recommends a separator design (FIG. 6 in the aforementioned API document) which at best is suited for removal of liquid slugs and large droplets, neither, of which cause frequent sampling problems. Furthermore, there is no provision for maintaining process source gas temperature. Liquid aerosol, which are the most frequent source of liquid entrainment, are not easily separated from sample gas by this "Knock-Out" type of GPA separator.

Conventional mechanical coalescer elements constructed of fibers, screens, etc. require gas flow thru the element for aerosol coalescing to occur. In most cases this precludes the return of the coalesced liquid to the process gas source at the original source pressure. With increasing environmental concerns disposal of the coalesced liquid can present serious problems if it cannot be returned to the original source.

Gas phase separation membranes are known and utilized in stack and flue gas analyzers for removal of entrained water, sub-micron aerosols, and filtration of ultra-fine particulates; examples of such membranes include the gas phase separation membranes utilized in the GENIE Series 100 line from A+ Corporation of Prairieville, La. USA. However, the utilization of said membranes is not believed contemplated in conjunction with the system of the present invention.

GENERAL SUMMARY DISCUSSION OF THE INVENTION

Unlike the prior art, the present, searched for invention provides a system for retrieving a gas phase sample from a gas stream containing entrained liquid, in a cost effective highly accurate, and generally easily implemented fashion, providing a gas sample at the prevailing process gas source pressure and temperature condition, thereby preventing gas phase composition changes. The subject invention, a sample conditioner assembly, provides a coalescer design that overcomes the problems associated with prior art systems, methods, and hardware.

The preferred embodiment of the present invention contemplates sample conditioning wherein there is provided a coalescing assembly particularly suited for coalescing, which employs a phase separating membrane for the removal of liquid entrained in sample gas.

In the first operating mode of the preferred embodiment of the present invention, this coalescing assembly is positioned external to the process source gas, and coalesced liquid separated by a phase separating membrane is returned to said process source gas by gravity free flow. In a second operating mode of this preferred embodiment of the present invention coalesced liquid, drained from the coalescing assembly, is disposed by piping to a location external to the original process source gas.

In accordance with a second embodiment of the present invention, the coalescing assembly is inserted into a housing, said housing and phase separating membrane portion of said coalescing assembly being positioned within the containment walls of a process source gas vessel or pipeline. A means is provided for inserting and withdrawing the coalescing assembly from said housing during which time said housing is inserted into a pressurized process source gas. This feature facilitates the inspection or replacement of the coalescing element which consists of a phase separating membrane.

Additionally, a valving means positioned in the lower end of said housing is actuated to a closed position by the withdrawal of said coalescing assembly which provides isolation and containment of the process source gas. Said second embodiment of the present invention has threaded means to facilitate said insertion and withdrawal of the coalescing assembly from said housing even when the process source gas is at elevated pressure.

In the third embodiment of the present invention, a pressure reducing regulator is integrated into said coalescing assembly of said second embodiment of the present invention.

In the preferred, second, and third embodiment of the present invention, the phase separation membrane employed repels aqueous and organic liquids while remaining permeable to gas.

Further, in the preferred, second, and third embodiment of the present invention, a support member, placed immediately upstream of said phase separation membrane protects the unit against physical damage which may otherwise occur if fluid flow is inadvertently reversed during a startup or shutdown operation.

A major advantage of the preferred, second, and third embodiment of the present invention over prior art, is that liquid entrained in a gas is removed at essentially the prevailing process gas source pressure and temperature condition, thereby preventing gas phase composition changes. A second advantage is that the insertion means, consisting of the rotation of a threaded member is safe, simple, and economical.

The advantage offered by the third embodiment is that pressure reduction or regulation occurs after entrained liquid has been removed thereby preventing gas phase compositional changes.

The system of the present invention may also be utilized in conjunction with conventional sampling and analyzation techniques including isokinetic sampling and gas chromatography analysis, for example, to discern the amount of entrained liquid in a gas stream. In this regard, a sample of the gas stream would be processed with the present invention to remove entrained liquid therefrom, and this data from this sample would be compared with data obtained on said gas stream utilizing traditional sampling techniques, thereby allowing the user to discern the amount and type of entrained liquids removed from the stream, thereby providing an enhanced analysis of the gas stream.

In the article *Effect of Entrained Liquid on Orifice Measurement* by V. C. Ting, as presented in the 1998 proceedings of the American School of Gas Measurement Technology (1998, pp 85–88), Dr. Ting recognizes that standard orifice meter measurement of gas flow in a gas stream can be affected by a small amount of liquid entrained in the orifice meter, thereby calling into question the accuracy of said technique, which is widely utilized and relied upon in the industry. Conversely, the present invention provides a relatively cost effective and reliable system to provide detailed analysis as to the amount and content of entrained liquid within a gas flow, allowing the user to compensate for said entrained liquids in discerning gas flow measurements, as well as providing a detailed inventory of the composition of entrained liquid of the gas flow.

It is therefore an object of the present invention to provide a sample conditioning assembly that provides a gas sample at the prevailing process gas source pressure and temperature condition, thereby preventing gas phase composition changes It is a further object of providing a method of sampling a gas from a gas stream having entrained liquid, wherein the gas sample is maintained at the prevailing process gas source pressure and temperature condition, thereby preventing gas phase composition changes.

It is another object of the present invention to provide a system for sampling gas from a gas stream which is more accurate, cost effective, and more easily implemented and maintained than prior art systems.

Lastly, it is an object of the present invention to provide a method for accurately sampling a gaseous hydrocarbon stream having entrained liquid therein, in order to accurately discern the properties thereof.

BRIEF DESCRIPTION OF DRAWINGS

For a further understanding of the nature and objects of the present invention, reference should be had to the following detailed description, taken in conjunction with the accompanying drawings, in which like parts are given like reference numerals, and wherein:

FIG. 18 is a close up view of the invention of FIG. 17.

DETAILED DISCUSSION OF THE INVENTION

Figure 1:
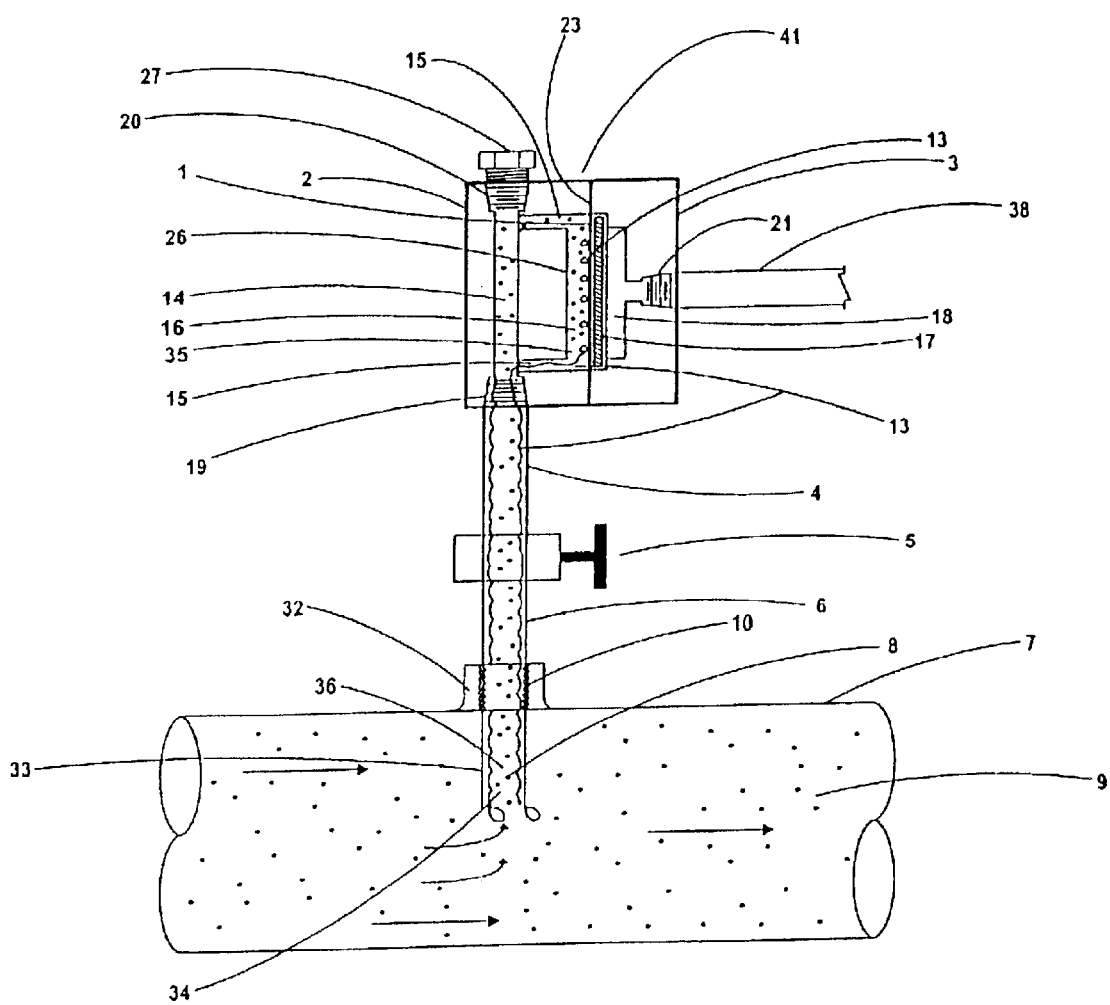
FIG. 1 is a side, cross sectional view of the first, preferred embodiment of the sample conditioning assembly of the present invention.
Figure 2:
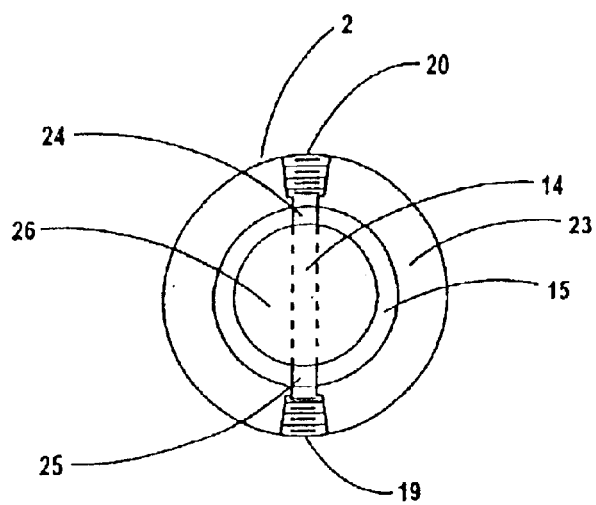
FIG. 2 is a side, cross sectional view of the invention of FIG. 1, illustrating the location of passage (14) relative to ports (19, 20), and groove (15).

Referring to FIGS. 1 and 2, the preferred, first embodiment of the invention contemplates a sample conditioning assembly 41, utilizing a circular sheet of phase separation membrane 1, inlet plate 2, and outlet plate 3, sample conduit 4, block valve 5, sample conduit 6, membrane support 17, and sample conduit 38.

A passage 14, located in inlet plate 2, extends between port 19 and port 20. A circular groove 15, in the outer face 23 of inlet plate 2, intersects passage 14 at point 24 and point 25. Membrane retention plate 26, formed on face 23 of inlet plate 2 is circumscribed by circular groove 15. Port 19, Port 20 and Port 21 are threadingly adapted for receiving sample conduit 4, sample conduit 38, and plug 27.

A segment 10 of sample conduit 6 is threadingly adapted for attachment to threaded member 32 located on containment wall 7 of process gas source 9. Block valve 5 is in series fluid communication with sample conduit 4 and sample conduit 6. Sample conduit Segment 33 of sample conduit 6 extends, thru containment wall 7, with its opening 34, into process gas source 9.

In relation to a first operation mode of said first embodiment, sample gas 36 of process gas stream 9, containing entrained small and aerosol sized liquid droplets 8, enters opening 34 of sample conduit segment 33, flows thru conduit 6, block valve 5, conduit 4, port 19, passage 14 and circular groove 15 then into inlet cavity 16, wherein the gas phase of sample gas 36 flows thru phase separating membrane 1, membrane support 17, outlet cavity 18, port 21, sample conduit 38 and thereon to an external analyzer, sample storage container or other sample conditioning component not shown. Liquid droplets 8, entrained in the gas phase, are rejected by phase separating membrane 1, wherein said droplets 8 coalesce into larger droplets and/or film 13, gravity flows into the lower end 35 of inlet cavity 16, circular groove 15 and flows downward thru port 19, along sample conduit 4, block valve 5, sample conduit 6, sample conduit segment 33, thru opening 34 and thereon into process gas source 9.

Empirical testing revealed that a liquid film, composed of 80% isopropanol and 20% water by volume, can flow downward in a gas conduit simultaneously with an air stream flowing upward thru said gas conduit at velocities not exceeding seventeen feet per second and provided that the internal diameter of said gas conduit is not less than 0.25 inches.

Figure 3:
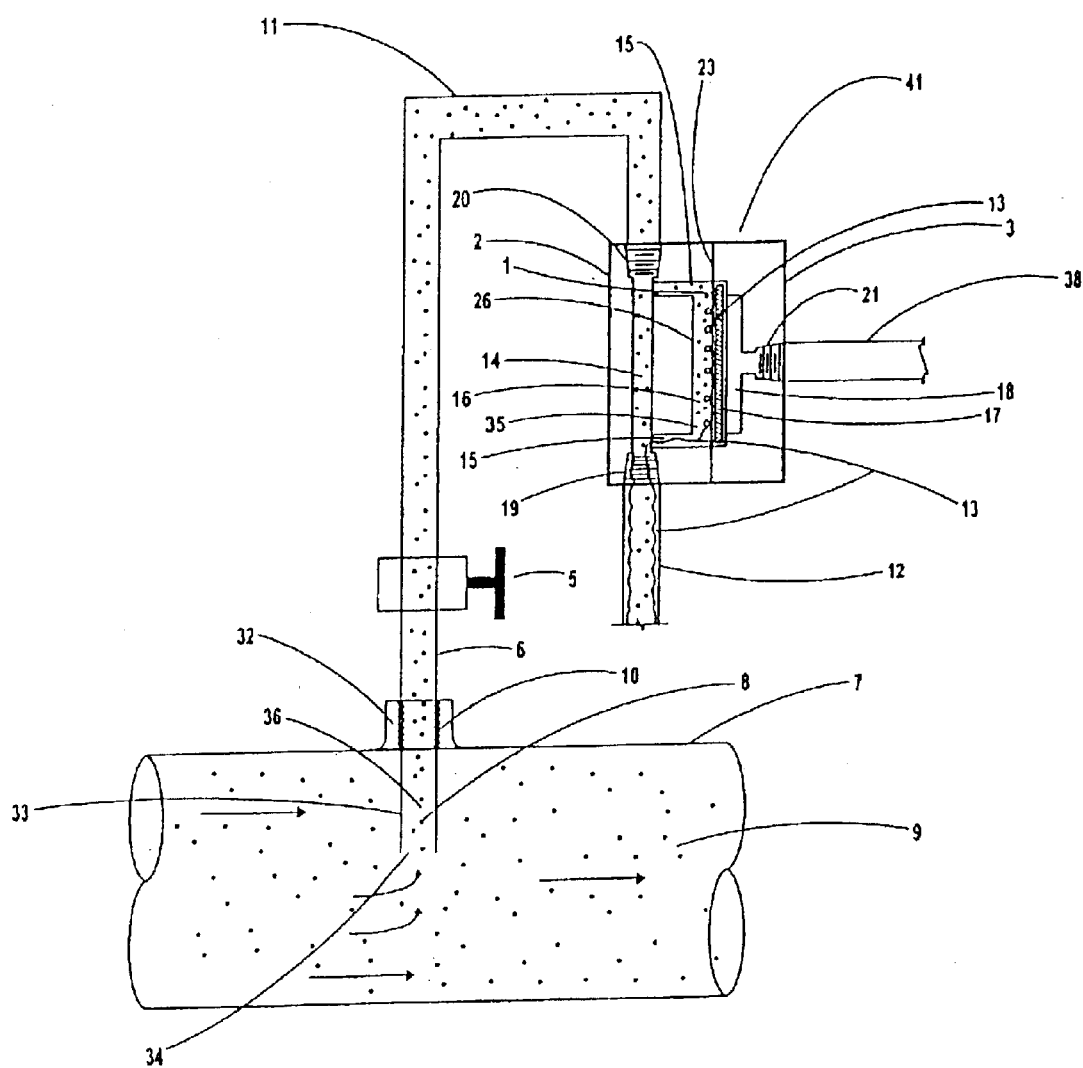
FIG. 3 is a side, cross, sectional view of the second operating mode of the preferred embodiment of FIG. 1, illustrating the operation thereof.

Referring to FIG. 3, a second operating mode of the first embodiment contemplates said first embodiment sample gas 36, of process gas stream 9, containing entrained liquid droplets 8, entering opening 34 of sample conduit segment 33, flowing thru conduit 6, blocking valve 5, and conduit 11, then entering port 20, flowing into passage 14, wherein a portion of said process gas flows thru circular groove 15, inlet cavity 16, phase separation membrane 1, membrane support 17, outlet cavity 18, port 21, sample conduit 38, and thereon to an analyzer, sample storage cylinder or other sample conditioning component not shown. Liquid aerosol droplets 8, entrained in the gas phase, are rejected by phase separation membrane 1, wherein it is coalesced into larger droplets and/or film 13, gravity flows into the lower end 35 of inlet cavity 16, circular groove 15 and into passage 14.

A second portion of said sample gas 36, containing entrained liquid droplets 8 and entering passage 14, from port 20, flows directly to port 19 wherein it combines with coalesced droplets and/or film 13, exits port 19, enters conduit 12, and thereon flows to an external destination not shown. Said second operating mode provides a means for removal of entrained liquid without distortion of the gas phase composition, decreases the sample transport time, and also provides an alternate method for disposal or analysis of coalesced entrained liquid when its return to the process gas source is not possible, necessary, or desirable. Passage 14 provides a means for bypassing a portion of sample gas 36, internal to coalescing assembly 41, said portion of sample gas 36 not being exposed to phase separating membrane 1.

Figure 4:
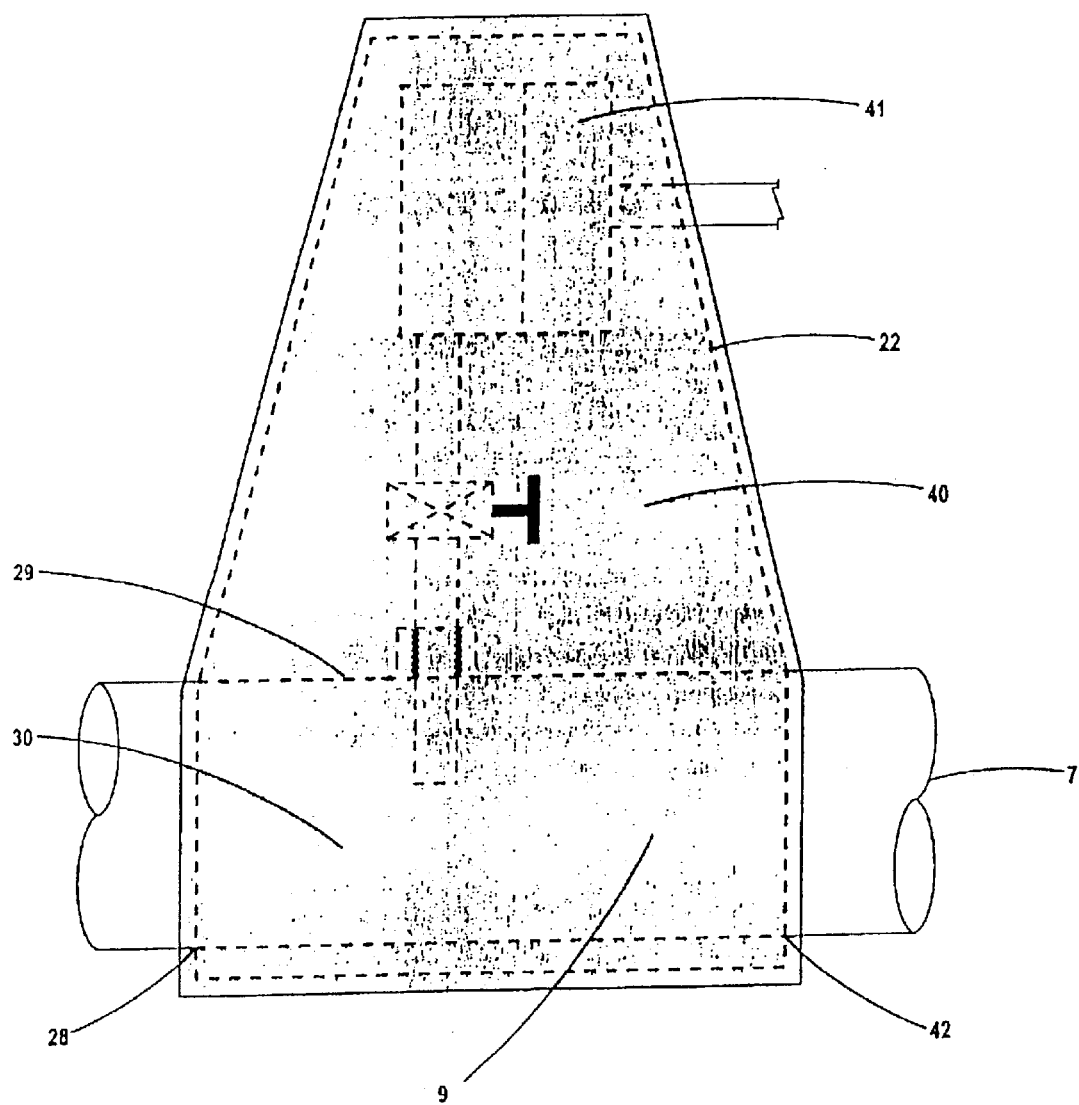
FIG. 4 is a side view of a housing configured to thermally insulate a coalescing assembly (shown in phantom).

In relation to the first and second operational modes of the first embodiment of the present invention, coalescing and removal of entrained liquid is accomplished at or near the prevailing process source pressure. To prevent gas phase distortion from occurring, the process of coalescing and removing of entrained liquid must also be carried out at essentially the prevailing process source temperature. There are several means by which a coalescing assembly may be maintained at essentially the prevailing process source temperature. One such means is shown in FIG. 4 and FIG. 5, where coalescing assembly 41 is shown internal to housing cavity 40 of thermally insulated housing 22.

Thermal insulation skirt 30 envelopes or surrounds process gas source vessel 7 from a first point 28 to a second point 42 laterally along said process gas source vessel 7. An insulated segment 29 of process gas source vessel 7 provides a means for exchange of heat between housing cavity 40 and process fluids 9. Heat exchange enhancement may be accomplished by several other means not shown which includes increase of thermal radiation surface by either increasing the area of uninsulated segment 29 or by employment of conventional heat sink attached to uninsulated segment 29.

Figure 5:
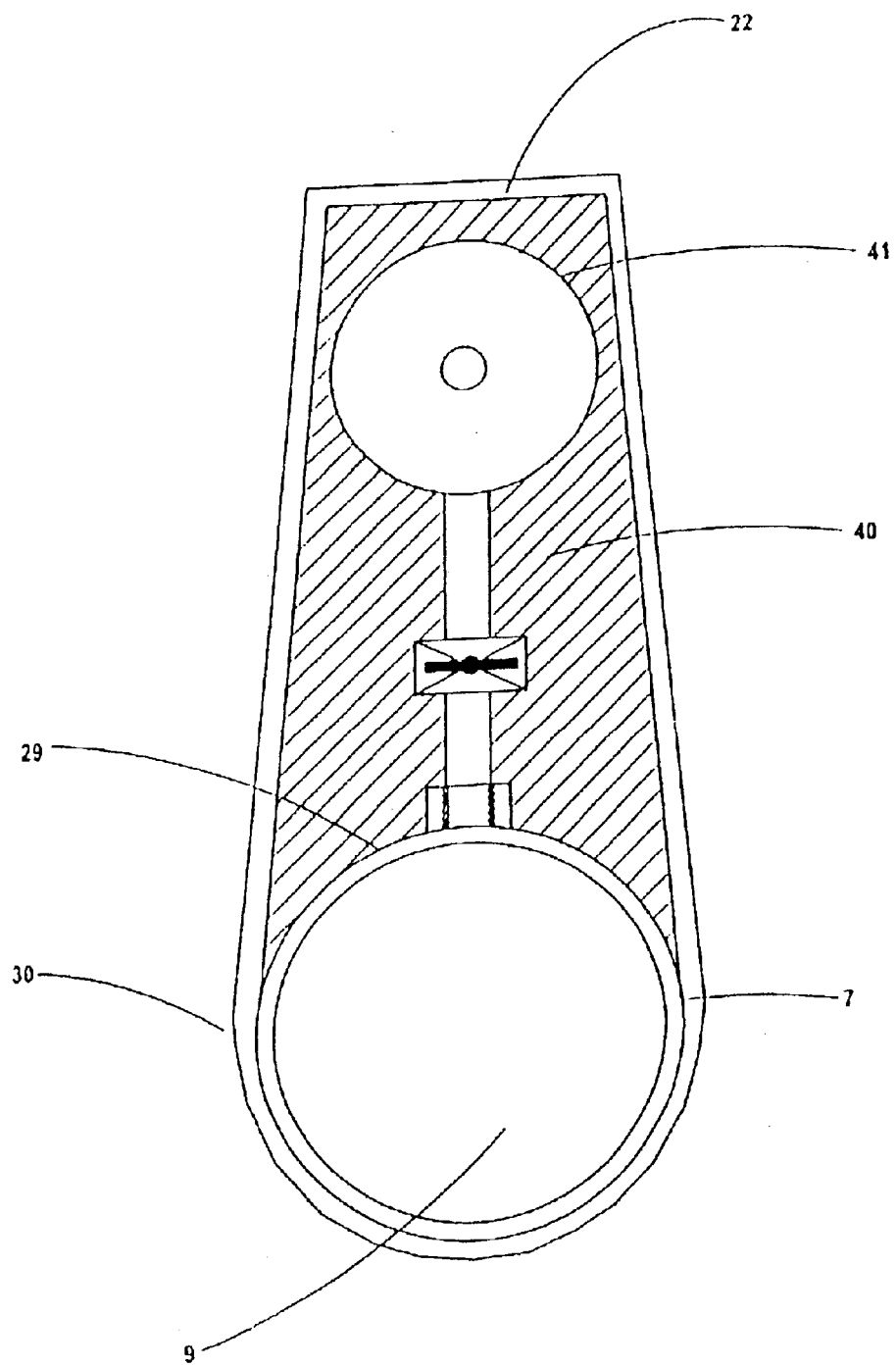
FIG. 5 is an end view of the illustration of FIG. 4
Figure 16:
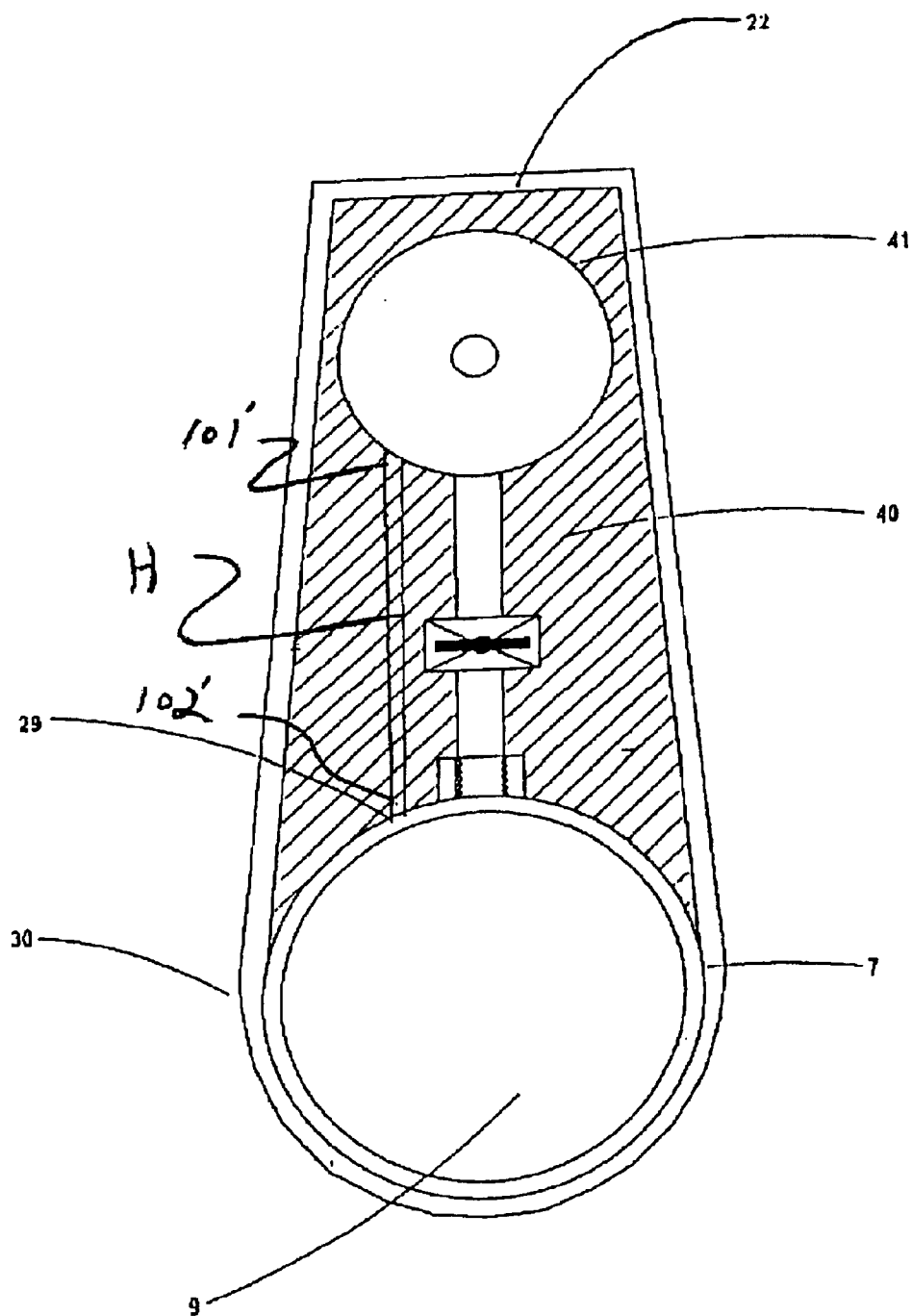
FIG. 16 is an illustration of FIG. 5, further indicating in phantom a heat pipe H running between the coalescing assembly and process gas source vessel.

Continuing with FIGS. 5 and 16, a heat pipe H (in phantom) having first 101' and second 102' ends, the first end communicating with the coalescing assembly, the second end communicating with the process gas source vessel 7 may also be employed singularly or in combination with other means for enhancement of heat transfer between housing cavity 40 and process fluids 9. Coalescing assembly 41, housed within housing cavity 40, will remain at essentially the temperature of process fluid 9, providing that there is sufficient heat transferred from process fluid 9 to housing cavity 40 to offset heat transfer thru insulated housing 22. Insulation skirt 30 permits uninsulated segment 29 to achieve essentially the temperature of process fluid 9 by negating the influence of the local ambient temperature.

FIGS. 6–8, 11–12, and 15 disclose a second embodiment 72 of the present invention, illustrating a housing assembly 43 and coalescing assembly 44. In combination, valve assembly 47 and housing 68 comprise housing assembly 43. Valve assembly 47 comprised of stem 48, poppet body 49, "O" ring 50, seat 51, spring 52, snap ring 53, washer 92, O ring 94, and valve housing 45, is attached to lower section 46 of housing 68 by male threads 54 and female threads 55. Coalescing assembly 44 is comprised of tubular stem 56, retaining bolt 57, porous membrane support 58, washer 65, phase separating membrane 59, O ring 60, O ring 61, rod 62, rod 63, snap ring 66, retaining washer 106, right threaded nut 64, and thrust washer 67. Rods 62 and 63 press fit into holes 92a and 92b (FIG. 7) respectively said holes being formed in the outer surface of tubular stem 56.

Figure 6:
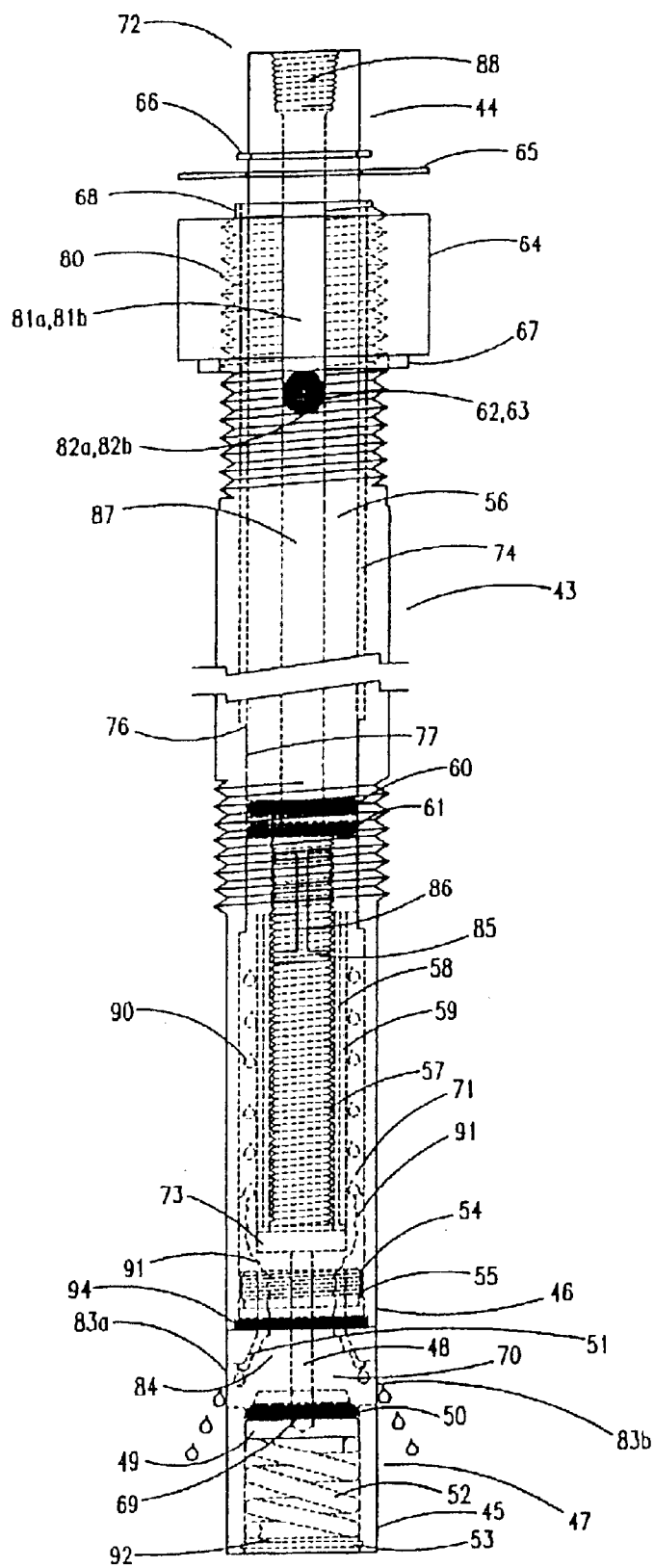
FIG. 6 is a side, partially cut-away, partially cross-sectional view of the second embodiment of the invention of FIG. 1, illustrating housing assembly (43) and coalescing assembly (44).
Figure 7:
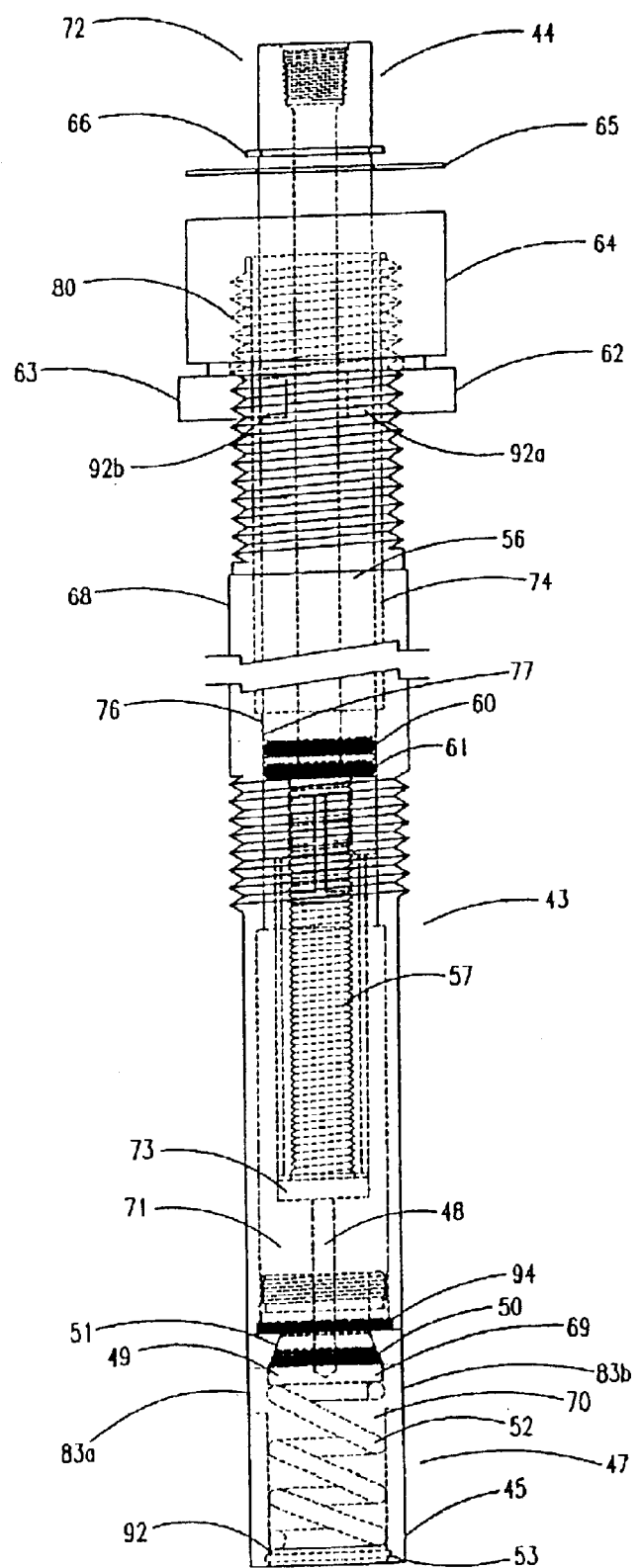
FIG. 7 is a side, partially cut-away, partially cross-sectional view of the invention of FIG. 6, illustrating the opening of poppet assembly (69) in an open position.
Figure 8:
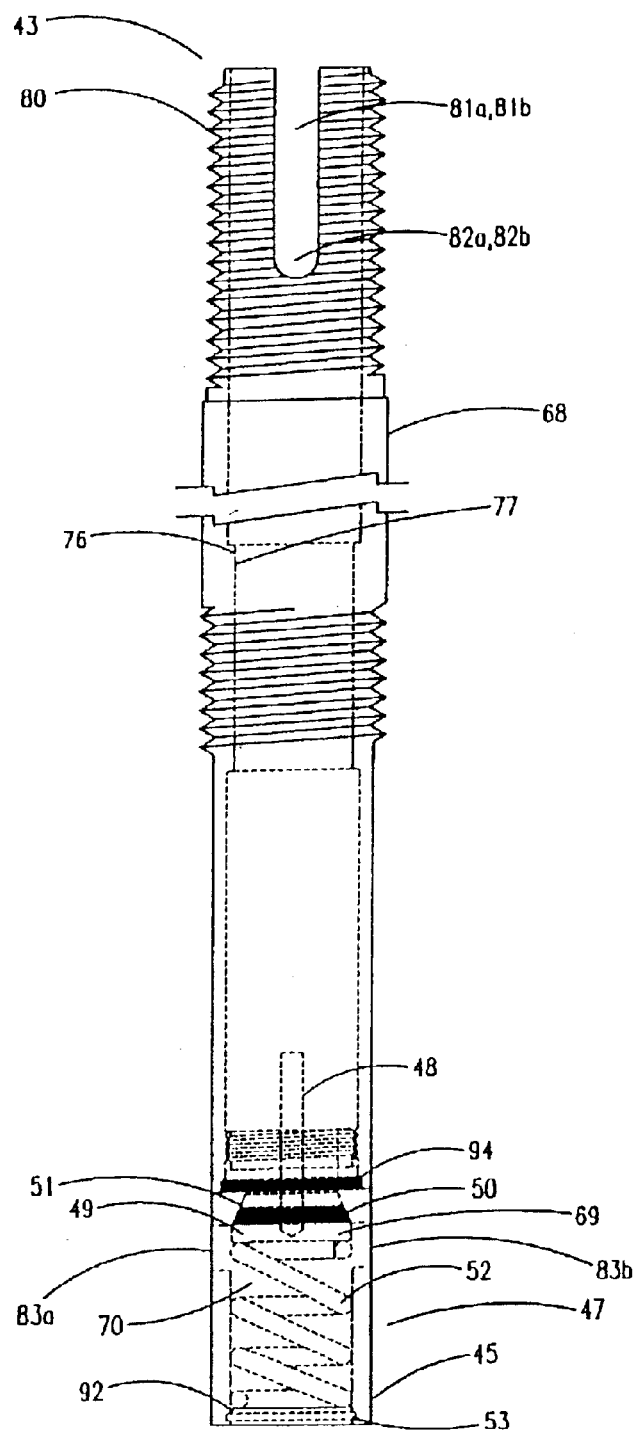
FIG. 8 is a side, partially phantom view of the invention of FIG. 6, illustrating the housing assembly (43) removed from the coalescing assembly (44).

With coalescing assembly 44 removed from housing assembly 43, as shown in FIG. 8, poppet assembly 69, comprised of stem 48, poppet body 49, and O ring 50; urged by the expansion of spring 52, travels upwards until contact of O ring 50 is made with seat 51, thereby forming a first fluid barrier between valve housing cavity 70 and membrane cavity 71 (FIGS. 6 and 7).

When coalescing assembly 44 is fully reinserted into housing assembly 43, as shown in FIG. 6, the downward force exerted by the head 73 of retention bolt 57 upon stem 48 forces poppet assembly 69 downward; thereby breaking contact between O ring 50 and seat 51 and reestablishing fluid communication between valve housing cavity 70 and membrane cavity 71.

Figure 9:
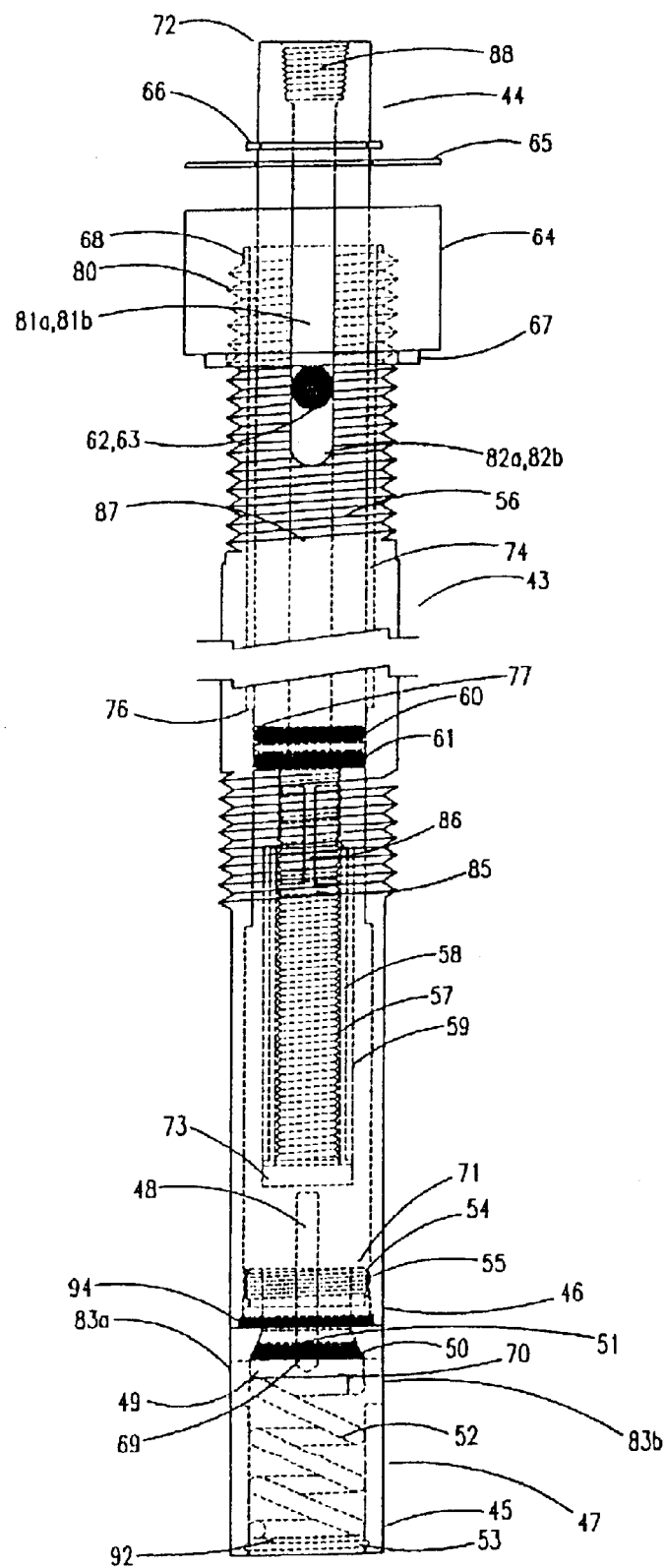
FIG. 9 illustrates a the invention of FIG. 8, with the internal components in phantom, affixed to coalescing assembly (44).

O ring 60 and O ring 61, in combination with inner wall 77 of housing 68 form a second fluid barrier between membrane cavity 71 and upper housing cavity 74, said fluid barrier being first formed during the insertion of coalescing assembly 44 into housing assembly 43 (Refer to FIG. 9), and at which time O ring 61 contacts inner wall 77 at point 76. When coalescing assembly 44 is inserted into housing assembly 43 until the head 73 of retention bolt 57 first contacts stem 48, as shown in FIG. 7, O ring 60 and O ring 61 are both in contact with inner wall 77 and form an effective said second fluid barrier between membrane cavity 71 and upper housing cavity 74, said second fluid barrier being formed before contact is broken between O ring 50 and seat 51.

Figures 10, 10A:
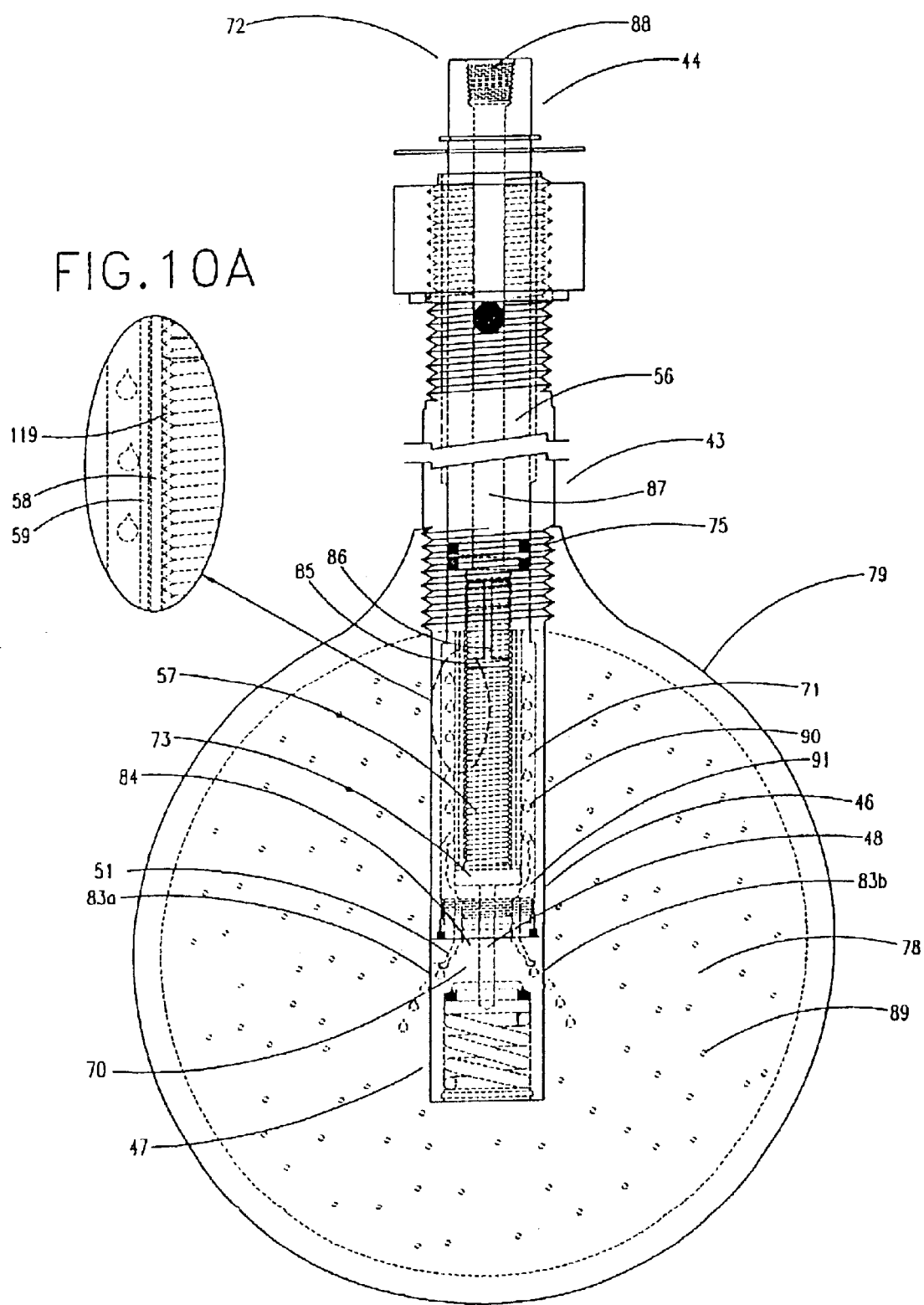
FIG. 10 illustrates the an end view of the invention of FIG. 6 installed into a pipeline having a fluid stream, wherein entrained liquid is shown draining from valve housing cavity, and wherein gas phase flows through phase separation membrane (59), up to an analyzer or storage container, etc.
Figure 11:
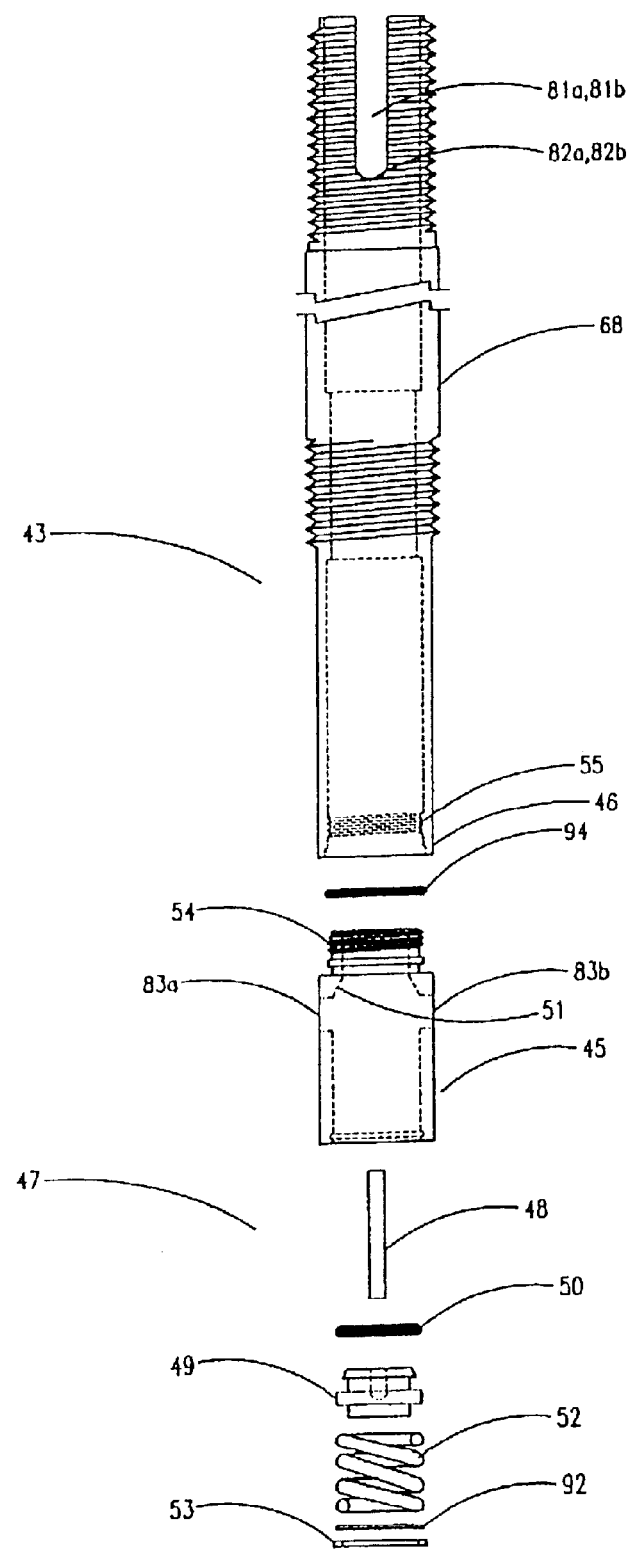
FIG. 11 is an exploded view of the sample conditioning assembly (72) of FIG. 10, illustrating the housing.
Figure 12:
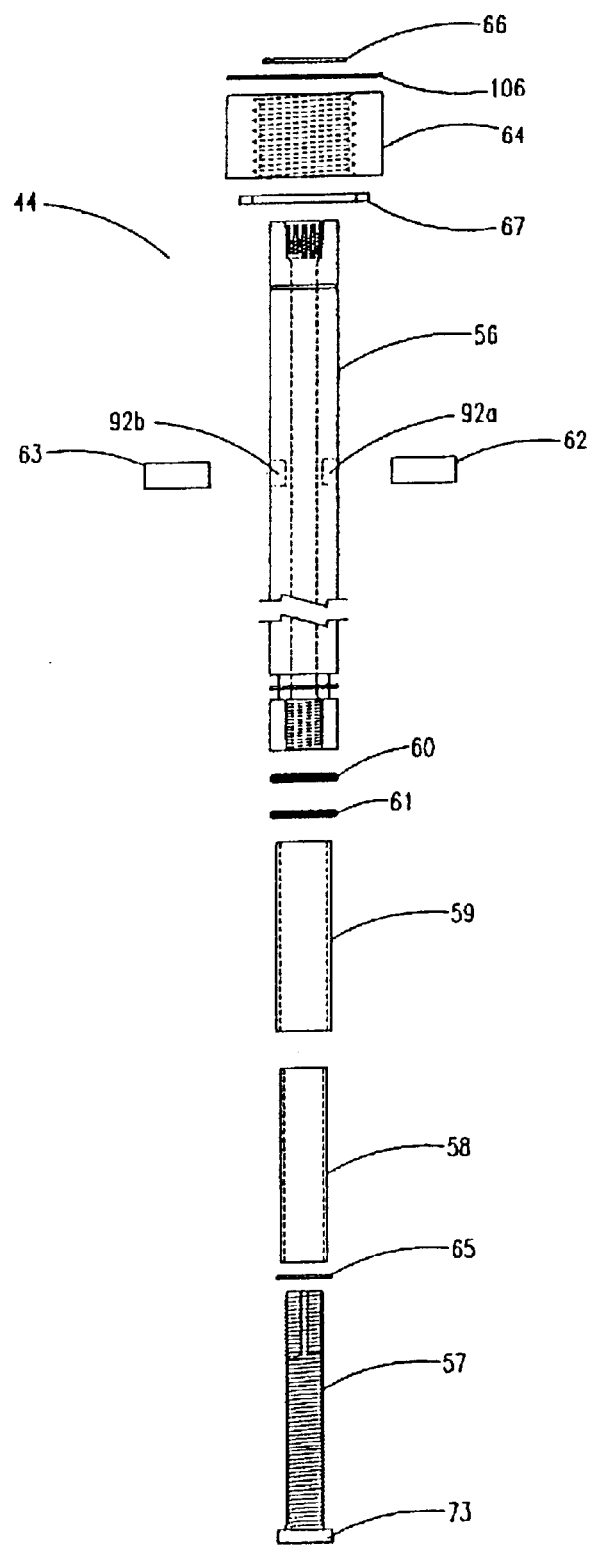
FIG. 12 is an exploded view of the sample conditioning assembly of of FIG. 11, illustrating the valve assembly, springs, membrane, and internal components.

The length relationship between coalescing assembly 44 and housing assembly 43 is such that said second fluid barrier is established at all times during insertion or withdrawal of coalescing assembly 44 to or from housing assembly 43 wherein O ring 50 is not in contact with seal 51 and fluid communication is established between valve housing 70 membrane cavity 71, and process gas source 78 (Refer to FIG. 10). Upper housing cavity 77, open to the atmosphere, is at or near atmospheric pressure.

Right threaded nut 64 (Refer to FIG. 6), when engaged with male threads 80 on housing 68 and rotated clockwise, exerts a downward force upon thrust washer 67, rod 62, rod 63, forcing the entire coalescing assembly 44 downward, thereby overcoming the upward force exerted by spring 52 and the action of process gas source 78 (Refer to FIG. 10) pressure against the lower surfaces of coalescing assembly 44.

Counterclockwise rotation of right threaded nut 64 facilitates the withdrawal of coalescing assembly 44 from housing assembly 43. Slot 81a and slot 81b in the wall of housing 68 guide rod 62 and rod 63 to prevent rotation of coalescing assembly 44 as it is inserted or withdrawn into or from housing assembly 43. Closed end 82a of slot 81a and closed end of 82b of slot 81b acting on rod 62 and rod 63, limit the downward travel of coalescing assembly 44 into housing assembly 43 to insure that spring 52 is not over compressed by overtravel of poppet assembly 69.

Figure 17:
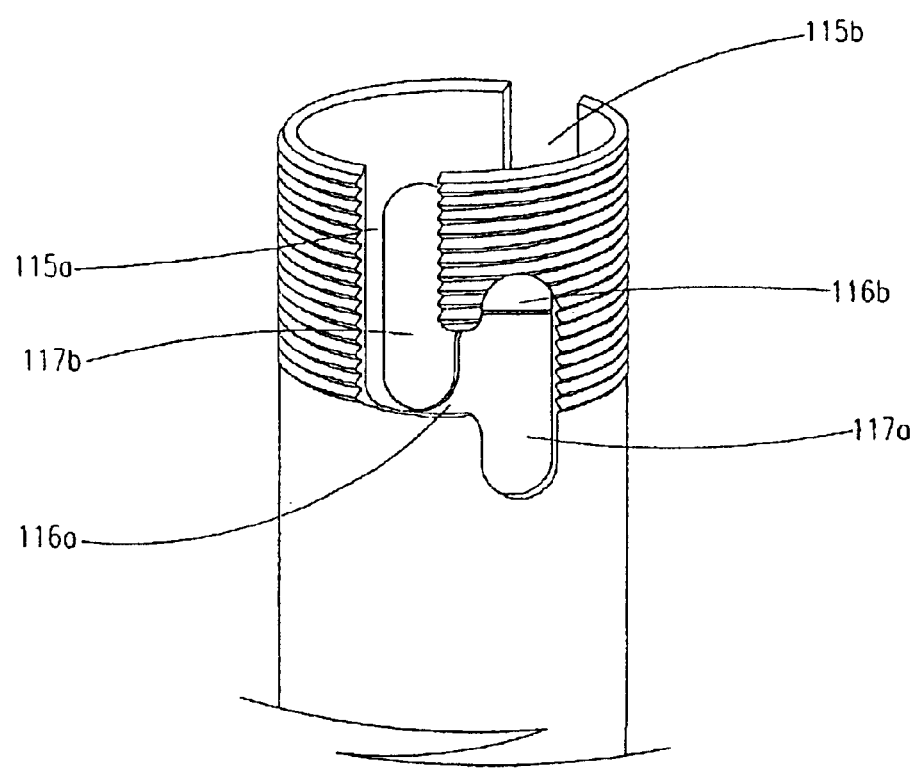
FIG. 17 illustrates an alternative design for construction of the rod guide slots (81) and (81b) in housing (68).

An alternate design for rod guide slots 81a and 81b is disclosed in FIG. 17 and FIG. 18. Slot 115a and slot 115b guide rod 62 and rod 63 in a vertical plane, slot 116a and slot 116b guide rod 62 and rod 63 in a horizontal plane, and slot 117a and 117b guide rod 62 and rod 63 in a vertical plane.

During insertion of coalescing assembly 44 or coalescing/pressure reducing assembly 95 into housing assembly 43, rod 62 enters slot 115a at its upper end 121a and rod 63 enters slot 115b at its upper end 121b. The downward movement of rods 62 and 63, resulting from the downward force exerted by nut 64 is limited by the lower ends 120a and 120b of slots 115a and 115b. In order for rods 62 and 63 to move further downward coalescing assembly 44 or coalescing/pressure reducing assembly 95 must be rotated counterclockwise, permitting rods 62 and 63 to traverse slots 116a and 116b and enter slots 117a and 117b wherein rods 62 and 63 can proceed downward until limited by lower ends 119a and 119b of slots 117a and 117b.

During the counterclockwise rotation of nut 64 to facilitate the withdrawal of coalescing assembly 44 or coalescing/pressure reducing assembly 95, rods 62 and 63 move vertically upward in slots 117a and 117b in response to the pressure exerted by process gas source 78, (refer to FIG. 10). When rods 62 and 63 reach midpoint 122a and midpoint 122b of slot 116a and slot 116b o-ring 50 contacts seat 51 thereby forming a fluid barrier between valve housing cavity 70 and membrane cavity 71 (FIGS. 6, 7, 17 and 18). Process gas source 78, trapped between the fluid barrier formed by o-ring 50 and seat 51 and the fluid barrier formed by contact of o-ring 60 and o-ring 61 with inner wall 77 (refer to FIG. 9) urges coalescing assembly 44 or coalescing/pressure reducing assembly 95 upward until rod 62 and rod 63 upward travel is limited by the upper end 118a and 118b of slot 117a and 117b. In this position rods 62 and 63 cannot be rotated clockwise in order to enter horizontal slots 116a and 116b. The pressure of process gas source 78 must be reduced by externally venting through outlet port 88 of coalescing assembly 44 or port 116 of coalescing/pressure reducing assembly 95 before coalescing assembly 44 or coalescing/pressure reducing assembly 95 can be lowered to a point where rod 62 and rod 63 can traverse horizontal slots 116a and 116b, and enter slot 115a and 115b wherein the withdrawal from housing assembly 44 can be completed.

The zig zag pattern of slots 115a, 115b, 116a, 116b, 117a and 117b in combination with rod 62 and rod 63 prevent removal of coalescing assembly 44 or coalescing/pressure reducing assembly 95 under conditions which are made unsafe by the upward force exerted by process gas source 78 acting upon coalescing assembly 44 or coalescing/pressure reducing assembly 95.

The aforementioned method disclosed for insertion and withdrawal of a coalescing assembly 44 and coalescing/pressure assembly 95 into a housing assembly 43 may also be applied for the insertion and/or withdrawal of any similar member into or from a similar housing which is inserted into a pressured fluid system.

Continuing with FIGS. 10 and 10A, in operation, sample conditioning assembly 72 is inserted thru and attached to pipe or vessel wall 79, and has its lower section 46 and valve assembly 47 immersed into a pressurized process gas source 78 as shown in FIG. 10. a small slip stream of process gas source 78 containing entrained liquid 89 enters valve housing cavity 70 by way of openings 83a and 83b, flows upward thru annulus 84, formed between the inner diameter of seat 51 and outer diameter of stem 48, then into membrane cavity 71, wherein the gas phase flows thru phase separating membrane 59, membrane support 58, threaded passage 119, which is formed by threads in retaining bolt 57, passage 85, passage 86, bore 87 of tubular stem 56, outlet port 88 and thereon to an external analyzer, sample storage container, or other sample conditioning component not shown. Entrained liquid 89, in the gas phase is rejected by phase separating membrane 59, coalesces into large droplets 90 and or film 91, wherein it gravity flows thru the annulus 84, into valve housing cavity 70, then thereon thru openings 83a and 83b thereby returning to process gas source 78.

The physical dimension relationship between the internal diameter of seat 51 and the outer diameter of stem 48 which form annulus 84, is sufficient to insure that coalesced liquid droplets 90 and film 91 can gravity flow downward thru said annulus 84 during which time a slipstream of process gas source 78 is flowing upward thru said annulus 84. Empirical testing has shown that an annulus of 0.10" formed between the internal diameter of seat 51 and the outer diameter of stem 48 having a minimum cross sectional area of 0.05 square inches is sufficient to conduct a downward flow of 10 cubic centimeters per minute of liquid film composed of 80% isproponal and 20% water by volume and an upward flow of gas at a velocity not exceeding 15 feet per minute.

Said liquid flow rate and gas velocity condition being satisfactory for the intended applications of sample conditioning assembly 72.

Phase separating membrane 1, of the first embodiment and phase separating membrane 59 of the second and third embodiment may utilize the a phase separation membrane as provided by A+ CORP of Prairieville, La., for example, type 6 membranes as utilized in the GENIE Series 100 membrane separators.

In order for a membrane to be useable in the separation of entrained liquid in sample gas as required by the present invention it must exhibit certain characteristics such as: (a) not becoming wetted by the entrained liquid, this characteristic is required for surface coalescing; (b) rejecting entrained liquid at the operating differential pressure across the membrane which is required to produce the desired gas flow rate thru the membrane, this characteristic is needed to prevent liquid flow thru the membrane; (c) having essentially the same permeability or flux rate for all components of a sample gas mixture, this characteristic is required to prevent alteration of the gas phase composition during its passage thru the membrane; (d) having sufficient gas permeability so that the required flow rate of sample gas thru the membrane can be produced at low membrane differential pressure, this characteristic is required to minimize the membrane area requirements.

Laboratory analysis, conducted by a gas chromatograph based BTU analyzer of pipeline quality natural gas sample, is shown in Table II.

TABLE II

Natural Gas Analysis in Mole % - Laboratory Analysis

|  | Analysis A | Analysis B | Analysis C |
| --- | --- | --- | --- |
| $C_6$ Plus | 0.4128 | 0.4188 | 0.4148 |
| Propane | 2.5814 | 2.5796 | 2.5789 |
| I - Butane | 0.9706 | 0.9694 | 0.9708 |
| N-Butane | 0.6714 | 0.6697 | 0.6710 |
| Neopentane | 0.0097 | 0.0098 | 0.0099 |
| I - Pentane | 0.3019 | 0.3001 | 0.3028 |
| N - Pentane | 0.1903 | 0.1881 | 0.1901 |
| Nitrogen | 0.1389 | 0.1354 | 0.1384 |
| Methane | 87.1946 | 87.2045 | 87.1967 |
| Carbon Dioxide | 1.4522 | 1.4522 | 1.4541 |
| Ethane | 6.0761 | 6.0727 | 6.0724 |
| Dry Gross BTU | 1154.39 | 1154.45 | 1154.42 |

Analysis A - Baseline analysis of natural gas sample utilized for analysis B,C,D, and E. - Sample gas did not flow thru a phase separation membrane.
Analysis B - Gas flowed thru A+ Corp Type 6 membrane from membrane source a. a bypass cross flow rate of 900 cc/min. also flowed simultaneously across the membrane surface.
Analysis C - Gas flowed thru A+ Corp Type 6 membrane from membrane source a. There was no bypass cross flow.

By comparing results of analysis A, B, & C, it can be seen that the A+ Corporation membrane Type 6 did not induce any appreciable changes in the composition or BTU value of natural gas sample flowing thru said membrane.

Tests were conducted on rich gas samples having BTU values of 1250 BTU and 1500 BTU by Southwest Research Institute, who is sponsored by the Gas Research Institute and overseen by American Petroleum Institute chapter 14.1 working group. The interim research results, issued in April 1998 by Southwest Research Institute, reflect less than 0.25%, distortion in gas density, (a reflection of the molecular weight) or heating value, (BTU value) in said 1250 BTU and 1500 BTU gas samples made to flow thru A+ Corp Type 6 membrane from membrane source a before entering the analyzer.

Field results, conducted on membrane from membrane source C and A+ Corp Type 6 membrane from source a supported the aforementioned laboratory analysis.

In addition to providing enhanced sampling of the gas sample from the fluid stream vis a vis removal of entrained liquid therefrom, the present system may be utilized to facilitate detailed analysis of the contents and amount of entrained liquid in the fluid stream, when coupled with traditional sampling techniques. The system of the present invention may also be utilized in conjunction with conventional sampling techniques including isokinetic sampling, to discern the amount of entrained liquid in a gas stream, utilizing a sample from said gas stream containing a proportionate amount of liquid as found in said gas stream. In this regard, a sample of the gas stream would be processed with the present invention to remove entrained liquid therefrom, and this data from this sample would be compared with data obtained on said gas stream utilizing traditional isokinetic sampling techniques, to obtain a gas sample containing an amount of liquid proportional to that contained in the source stream, allowing the user to discern the amount and type of entrained liquids removed from the stream, thereby providing an enhanced sampling of the gas stream.

In practicing the method of discerning the contents and amount of entrained gas in the fluid stream utilizing the system of the present invention, one may: 1) perform conventional analysis of the fluid stream utilizing isokinetic or other analysis technique to discern the velocity and mass of the components of the stream; 2) sample said fluid stream utilizing the apparatus of the present invention, providing sample gas having the entrained liquid removed therefrom; and 3) applying comparative analysis of the data from (1) and (2) to discern the amount of entrained liquid removed from the gas, thereby discerning the liquid to gas ratio, liquid mass, composition, quantity, quality, and BTU value of the stream, of a combined or homogeneous stream.

A similar method of method of discerning the composition or amount of entrained fluid in a fluid stream containing vapor and entrained liquid, could include for example, the steps of:

a. obtaining a first representative sample of said fluid stream containing both vapor and entrained liquid in amounts representative of said fluid stream at prevailing temperature and pressure conditions;

b. obtaining a second representative sample of gas in vapor phase from said fluid stream, under prevailing temperature and pressure conditions;

c. vaporizing said entrained liquid in said first representative sample, while maintaining said vapor present in obtaining said first representative sample, so as to produce a homogeneous vapor phase sample;

d. analyzing said second representative sample, providing vapor phase data on vapor in said fluid stream at prevailing pressure and temperature conditions;

e. analyzing said homogenous vapor phase sample, obtaining homogenous vapor/liquid data on the composition of said fluid stream;

f. comparing said vapor phase data and said vapor/liquid data, and discerning the differences thereof.

This method could be utilized to discern the amount, or composition of entrained liquid present in said fluid stream.

Gas chromatography may well be a preferred method of analysis in this regard, although various conventional methods exist, some of which may be preferable over others, depending upon the circumstances.

Another alternative analysis under the invention of the present system could include collecting the liquid drained from the membrane area, allowing the user to measure the amount and composition of said entrained liquid in the fluid stream.

A third embodiment 106 of the present invention, (Refer to FIG. 13 and FIG. 14) is comprised of aforementioned housing assembly 43 and coalescing/pressure reducing assembly 95. Said coalescing/pressure regulator assembly 95 is comprised of tubular stem 96, rod 97, ball 98, spring 99, nut 107, lower housing 100, upper housing 101, diaphragm 102, spring 103, and handle 105, retaining bolt 57, washer 65, membrane support 58, phase separating membrane 59, O ring 60, O ring 61, rod 62, rod 63, right threaded nut 64, and thrust washer 67. In addition to the coalescing and entrained liquid removal function provided by second embodiment 72, said third embodiment 106 provides the additional function of pressure regulation.

A small slip stream of process source gas 78, at process gas source pressure and made free of entrained liquid by the second embodiment coalescing process previously described, exits passage 86 thru a center hole in nut 107, enters spring cavity 108, flows between ball 98 and seat 110, passage 112, then thru annulus 109 formed by the outer diameter of rod 97 and inner diameter of cavity 113 of tubular stem 96, enters diaphragm cavity 114 and then exits by flowing thru passage 115, port 116, and conduit 117 thereon to an external analyzer or sample storage means not shown.

The pressure of sample gas in diaphragm cavity 114 acting against diaphragm 102 produces an upward force against spring 103. The decompression of spring 52 produces an upward force against ball 98, lower rod segment 111, and rod 97 which serves to maintain contact between rod 97 and diaphragm 102. Handle 105 has a right threaded member 104 which is threadingly engaged in female threads 118. The gas pressure in passage 112, annulus 109, and diaphragm cavity 114 is regulated by altering the distance between ball 98 and seat 110. In operation handle 105 is rotated clockwise to increase or counter clockwise to decrease the gas pressure set point.

Rotation of the handle clockwise compresses spring 103 thereby increasing the downward force applied to the upper surface of diaphragm 102. Said downward force, acting upon the diaphragm 102, rod 97, lower rod segment 111 forces ball 98 downward, thereby increasing its distance from seat 110 resulting in greater gas flow into diaphragm cavity 114 and increasing the gas pressure at all points downstream of ball 98 and seat 110. Said increase in pressure results in increasing the upward force exerted by diaphragm 102 against spring 103. When the upward force resulting from the gas pressure acting on diaphragm 102 is equal to the downward force exerted by spring 103 the gas pressure is deemed to be at its set point. Changes in flow rate thru conduit 117 results in a momentary gas pressure change in diaphragm cavity 114.

Said momentary pressure change causes a movement of diaphragm 102 in a direction and magnitude which will change the distance relationship between ball 98 and seat 110 and restore the gas pressure to its set point.

The aforementioned pressure regulation method and its many variations are well known to those skilled in the art and it is also well known that gas pressure regulators which can be inserted into a pressurized vessel are commercially available. Two well known sources of these insertion type of gas regulators are Welker Engineering Company of Sugarland, Tex. and YZ Industries of Snyder, Tex.

Insertion gas pressure regulators are typically utilized for preventing condensation of hydrocarbons resulting from the Joule-Thompson cooling which occurs during the pressure reduction of a gas. The insertion gas pressure regulator's design provides for the pressure letdown to occur in a segment of said pressure regulator which is inserted in the gas source vessel. The gas surrounding said segment of the gas pressure regulator functions as a heat sink and prevents the gas temperature from lowering excessively during said pressure letdown.

However there is no provision in said pressure regulators for coalescing and removing aerosol droplets from the gas before pressure letdown occurs. As previously mentioned, the presence of liquid in any droplet size or form in a sample gas undergoing either a pressure or temperature change will change the gas phase composition. Mr. Thomas F. Welker, of Welker Engineering Company, in a presentation made at the American School of Gas Measurement Technology in Houston, Tex. in September of 1997, teaches that liquid contaminates may be put in flight by high turbulence in the source gas and that said contaminates may then become ingested into the probe regulator (another term for insertion type of gas pressure regulator) and thereby become part of the sample. He further teaches that said liquid contaminates should not become a part of the sample gas stream and should therefore not be analyzed. His teachings are consistent with aforementioned API and GPA recommended standard practices.

The major benefit of the third embodiment of the current invention is that it provides a means for removal of entrained liquids at prevailing process pressure and temperature, before reduction of the gas pressure. Said gas pressure reduction being performed in a region within probe housing 43 whereby heat sinking to the process gas source or its containment wall occurs.

Figure 13:
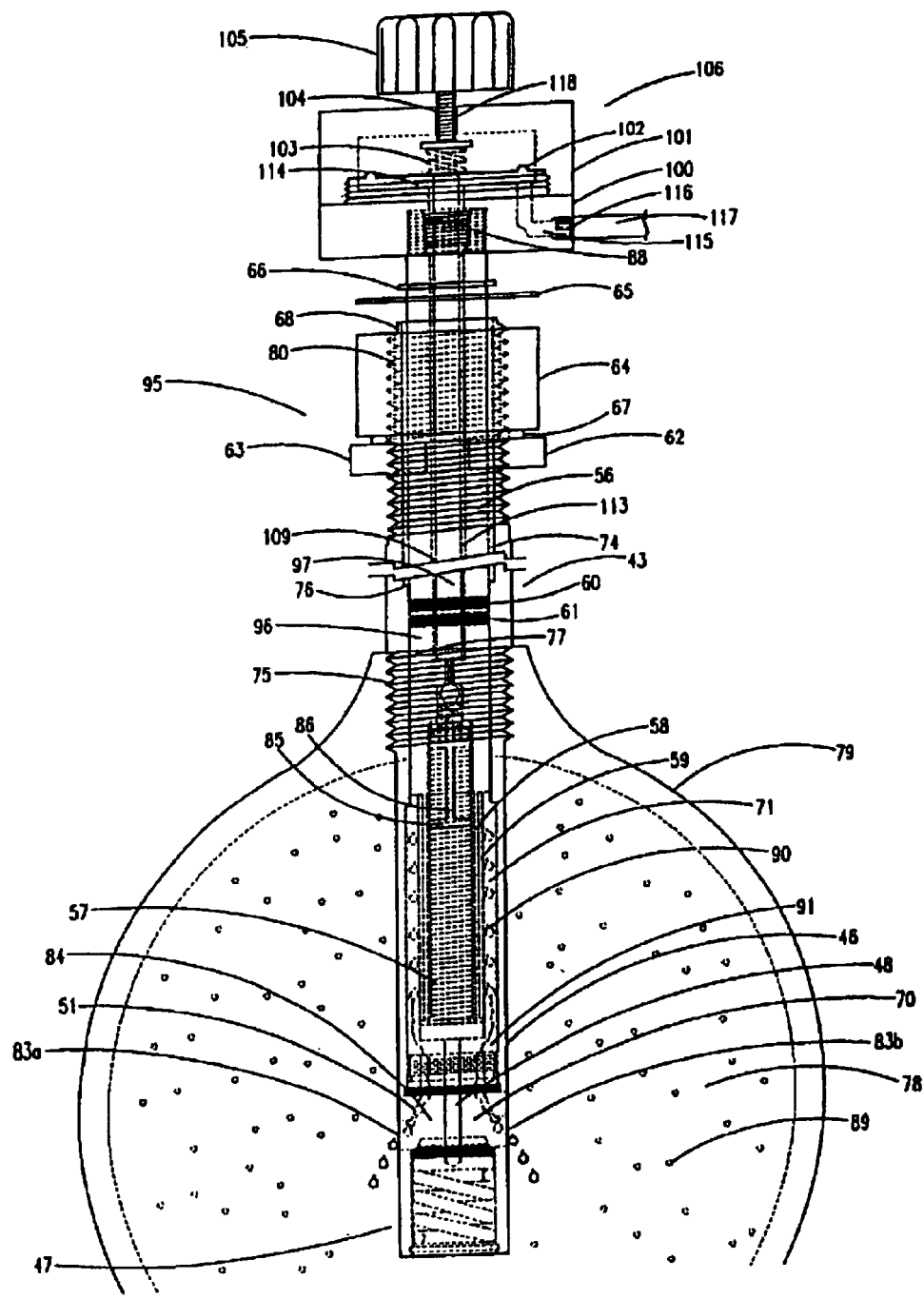
FIG. 13 is a partially cut-away, partially cross-sectional, side view, illustrating a third embodiment of the invention of FIG. 1, providing pressure regulation.
Figure 14:
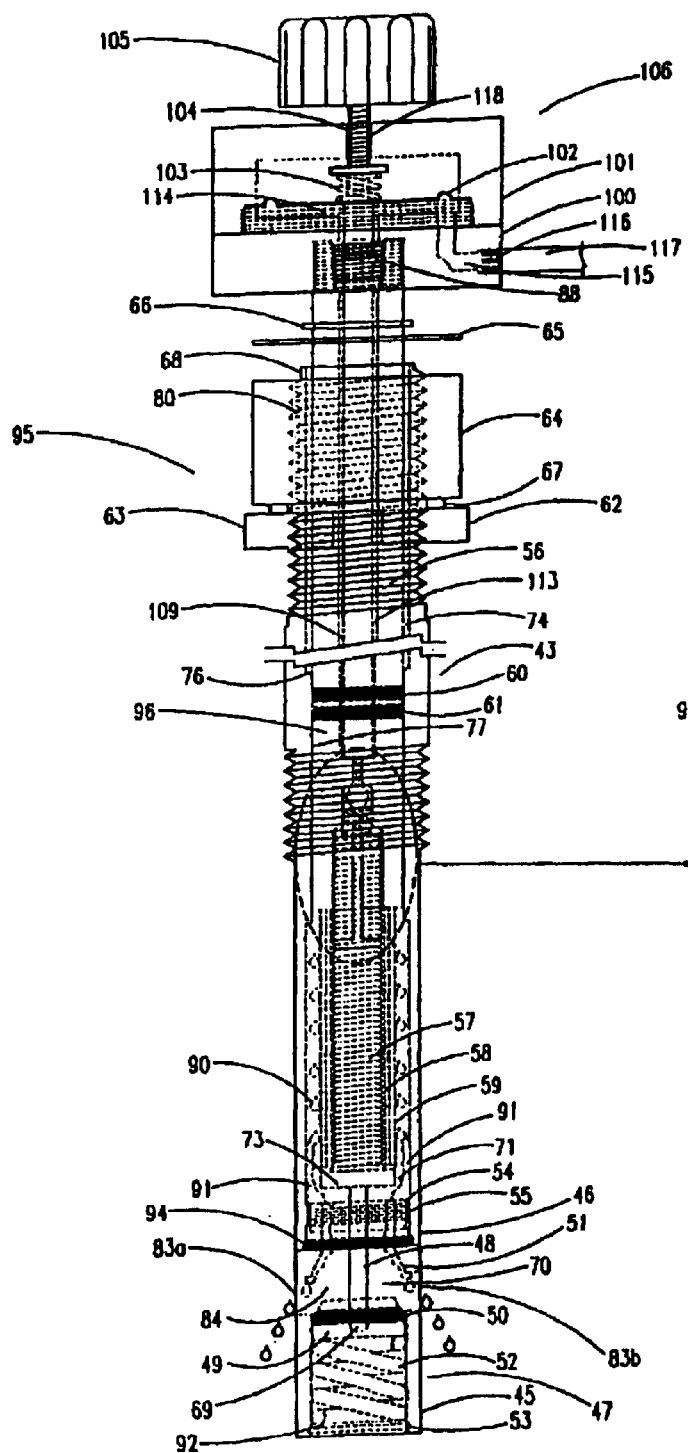
FIG. 14 is a partially cut-away, partially cross-sectional, side view, illustrating the invention of FIG. 13, indicating in phantom the area of FIG. 14A.
Figure 14A:
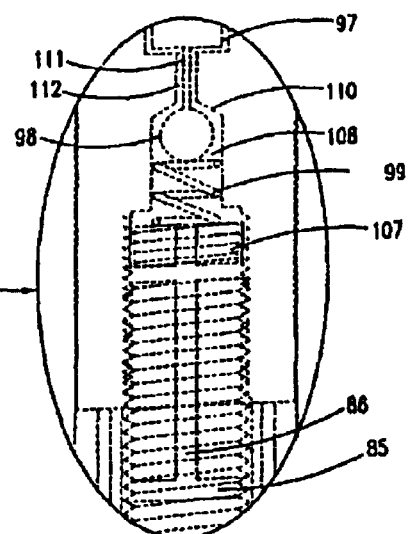
FIG. 14A is a side, partially cross-sectional, partially cut-away view of an area indicated in FIG. 14.
Figure 15:
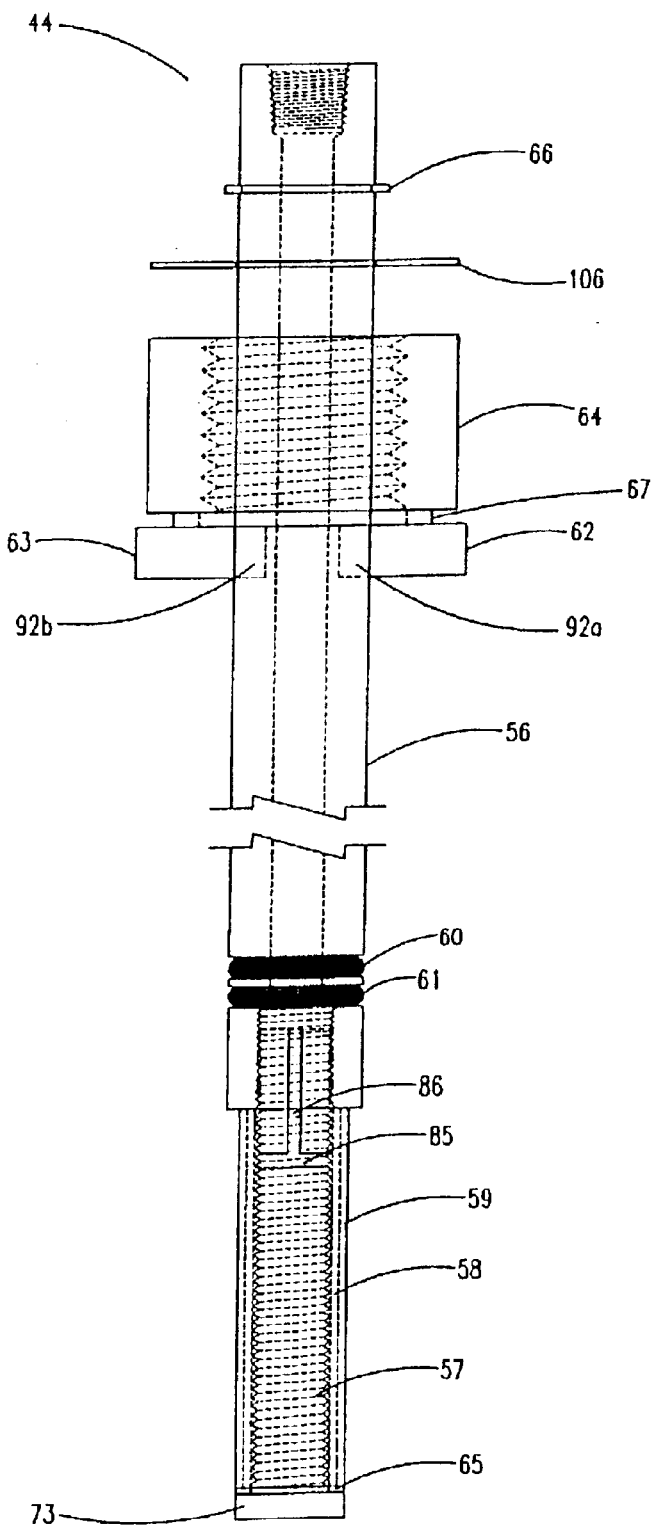
FIG. 15 is a side, partially cut-away, partially cross-sectional, assembled view of the invention of FIG. 12.

In FIG. 13 it can be seen that the ball 98 and seat 110 are in close proximity to threaded engagement area 75 of housing 43 to vessel 79. This approach prevents flashing of entrained liquids, which causes gas phase alteration, and minimizes cooling of the gas during pressure reduction which prevents condensation of some gas phase components and additional gas phase alterations.

The invention embodiments herein described are done so in detail for exemplary purposes only, and may be subject to many different variations in design, structure, application and operation methodology. Thus, the detailed disclosures therein should be interpreted in an illustrative, exemplary manner, and not in a limited sense.

What is claimed is:

1. A method of conditioning a sample of gas derived from a fluid stream, comprising the steps of:
   a. providing a fluid conduit having first and second ends, said first end of said fluid conduit communicating with said fluid stream;
   b. providing an insertion assembly comprising a phase separation membrane having first and second sides;
   c. providing a housing in communication with said fluid stream, said housing configured to receive said insertion assembly;
   d. inserting said insertion assembly into said housing;
   e. directing said sample of gas having liquid entrained therein to communicate with said phase separation membrane;
   f. allowing the passage of gas from said sample of gas through said phase separation membrane, providing filtered gas, while preventing the passage of entrained liquid from said sample of gas and coalescing said entrained liquid from said sample of gas.

2. The method of claim 1, wherein there is provided the additional step after step "e" of draining said coalesced liquid from the vicinity of said phase separation membrane.

3. The method of claim 2, wherein said coalesced liquid is drained into said fluid stream.

4. The method of claim 2, wherein there is provided the additional step after step "e" of analyzing said filtered gas.

5. The method of claim 2, wherein said fluid stream and said sample of gas has a temperature and a pressure, and wherein there is further included the step of maintaining said pressure and temperature of said sample of gas at the same temperature and pressure of said fluid stream.

6. The method of claim 5, wherein there is provided the additional step of providing a housing assembly comprising thermal insulation means, and wherein said housing assembly is configured to envelope said fluid conduit, said sample of gas, and said phase separation membrane so as to maintain said temperature of said sample of gas at the same temperature of said fluid stream.

7. The method of claim 2, wherein there is further provided containment means for containing said fluid stream, and wherein said fluid conduit, said phase separation membrane, and said drainage means are situated within said containment means.

8. The method of claim 2, wherein after step "e" there is provided the additional step of measuring the amount of coalesced liquid emanating from said drainage means.

9. The method of claim 2, wherein there is further provided the steps, after step "f" of:
   i. obtaining a representative sample of fluid from said fluid stream, said representative sample containing both gas phase and entrained liquid phase matter in equal proportion to said fluid stream;
   ii. vaporizing said entrained liquid contained within said representative sample to a produce a homogenous vapor phase sample; and
   iii. analyzing homogenous vapor phase sample, providing compositional data, and comparing same with said filtered gas analysis data, so as to discern differences therein.

\* \* \* \* \*

UNITED STATES PATENT AND TRADEMARK OFFICE
CERTIFICATE OF CORRECTION

PATENT NO. : 6,904,816 B2
DATED : June 14, 2005
INVENTOR(S) : Mayeaux

It is certified that error appears in the above-identified patent and that said Letters Patent is hereby corrected as shown below:

Title page,
Item [60], Related U.S. Application Data, change "and" to -- which is --.

Signed and Sealed this

Thirty-first Day of January, 2006

JON W. DUDAS
*Director of the United States Patent and Trademark Office*